Jan. 3 , 1956 E. J. GARDNER Plant Pat. 1,443

LILAC PLANT

Filed May 25, 1953

WITNESS

Addison E Avery

INVENTOR

EDWARD J. GARDNER, DECEASED,
BY ROBERT L. GARDNER, EXECUTOR

Wheeler, Wheeler & Wheeler
ATTYS.

United States Patent Office

Plant Pat. 1,443
Patented Jan. 3, 1956

1,443

LILAC PLANT

Edward J. Gardner, deceased, late of Horicon, Wis., by Robert L. Gardner, executor, Horicon, Wis., assignor to Robert L. Gardner Application May 25, 1953, Serial No. 357,395

1 Claim. (Cl. 47—60)

This invention pertains to a new variety of lilac (*Syringa vulgaris*) plant having large and relatively open trusses of single four petaled florets of light lavender color, each petal having a darker mid-stripe outlined in white to give the effect of a conspicuous cross on each floret.

Figures 1, 2:
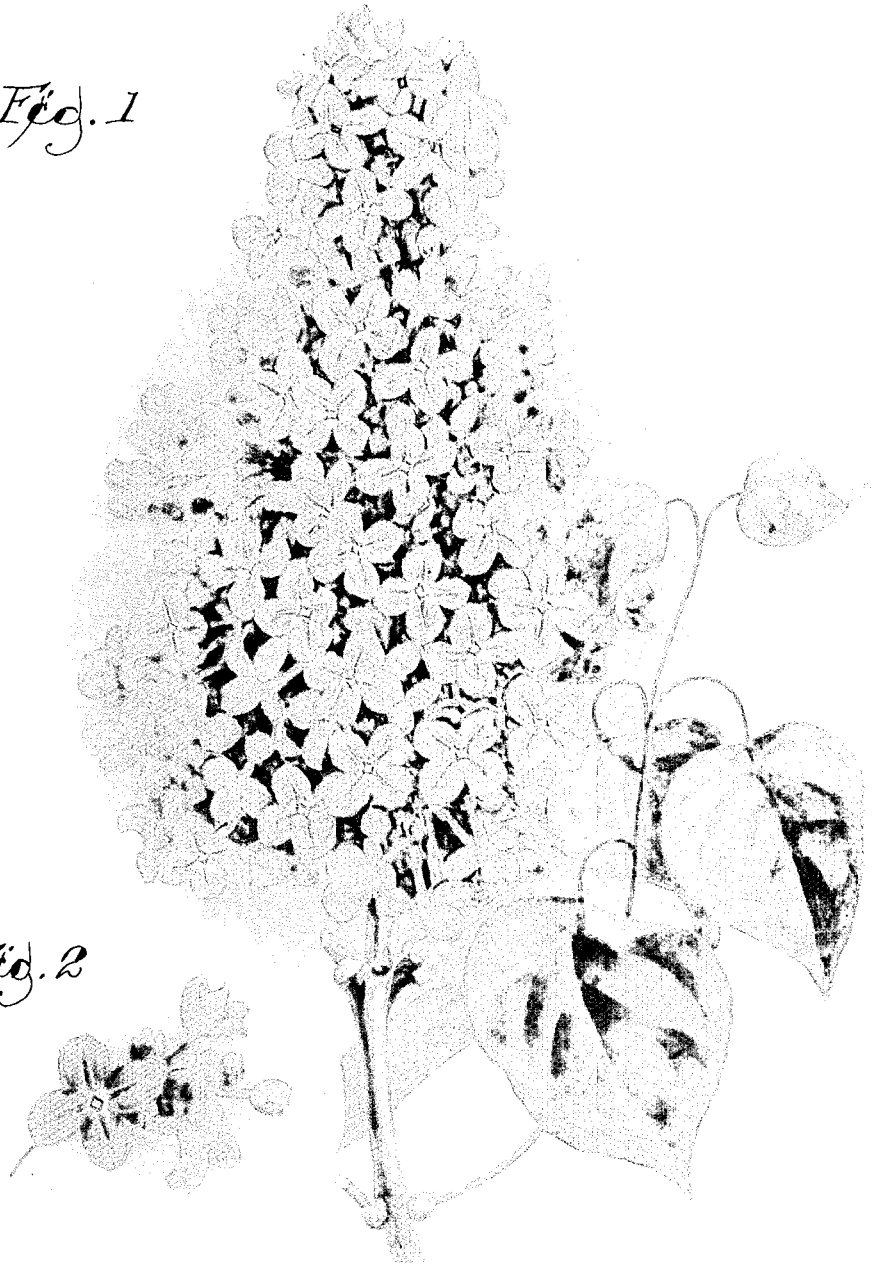
Fig. 1 is a view showing a single panicle of bloom with associated stem and leaves.
Fig. 2 is an enlarged detail view of a typical floret as it appears when fully open, adjacent florets being shown in bud and in partially opened form.

The original bush was a seedling of unknown ancestry, one of a number of lilac plants raised from mixed seed of uncontrolled pollination collected from choice varieties in my nursery. The original bush has been asexually reproduced by rooting cuttings therefrom at Horicon, Wis.

The lilac bush is similar to the bushes of other lilacs. The face of each leaf is green (Maerz and Paul, Dictionary of Color, Plate 22–K–8). The obverse or back side of each leaf is tinged with olive (Maerz and Paul, Dictionary of Color, Plate 21–J–7).

The bloom panicles are quite open, the florets being for the most part separately displayed and unobscured by their neighbors. Each floret is single and has four petals which are very broadly ovate as clearly shown in Fig. 2. In the open floret, the petals are substantially flat and in a common plane to which the axis of the calyx is at right angles. The buds are definitely a reddish purple (Maerz and Paul, Dictionary of Color, Plate 43–K–6), but in the open flowers the background color of the several petals is quite uniform and of the shade shown in Maerz and Paul, Dictionary of Color, Plate 42–F–6.

The time of bloom is mid-season. Both the buds and the blooms are exceptionally large. Individual florets measure one inch in diameter and more and the panicles are of considerably greater than average size. The lilac is fragrant but much less so than others. While the fragrance faintly suggests typical lilac fragrance, it is also reminiscent of some stronger odor which is somewhat comparable to lily-of-the-valley.

The reproductory organs of the individual florets are extremely compact and minute in relation to the size of the floret. The stamen anthers are golden-yellow and two in number and there is a single pistil which is of a yellow color having more green in it than does the stamen anthers.

The calyx is small and from it radiate lines of white on the bases of the several petals. Centrally of each petal, and extending radially from the calyx, there is a very well defined stripe darker and more blue than the background color of the petal, its color being identified in Maerz and Paul Dictionary of Color by Plate 42–B–7. Two of the white lines above referred to extend outwardly along the sides of the stripe to delineate it sharply from the background color of the petal. The result is a well defined cross on each four-petaled floret, each arm of which is formed by one of the stripes aforesaid, outlined in white on the individual petals, all as shown in Fig. 2 and indicated in a more general way in Fig. 1.

Having thus described some of the outstanding identifying characteristics of the lilac of my invention, I claim:

A new and distinct variety of lilac plant as described and illustrated and characterized by loose panicles of large single florets generally lilac in color, each floret comprising four petals, the respective petals having well defined stripes darker and more blue than the remainder of the petal and radiating from the center of the floret and outlined in white to present a distinct cross on each floret.

No references cited.